(12) United States Patent
Melzner et al.

(10) Patent No.: US 10,345,314 B2
(45) Date of Patent: Jul. 9, 2019

(54) LATERAL FLOW MEMBRANE ARRANGEMENT AND LATERAL FLOW IMMUNOASSAY DEVICE COMPRISING THE SAME

(71) Applicant: SARTORIUS STEDIM BIOTECH GMBH, Göttingen (DE)

(72) Inventors: Dieter Melzner, Göttingen (DE); Denise Van Rossum, Adelebsen (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 0 days.

(21) Appl. No.: 14/910,711

(22) PCT Filed: Apr. 29, 2014

(86) PCT No.: PCT/EP2014/001151
§ 371 (c)(1),
(2) Date: Feb. 8, 2016

(87) PCT Pub. No.: WO2015/018467
PCT Pub. Date: Feb. 12, 2015

(65) Prior Publication Data
US 2016/0178640 A1    Jun. 23, 2016

(30) Foreign Application Priority Data

Aug. 8, 2013 (EP) .................................... 13003965

(51) Int. Cl.
*G01N 1/00* (2006.01)
*G01N 33/68* (2006.01)
(Continued)

(52) U.S. Cl.
CPC ............. *G01N 33/689* (2013.01); *B05D 1/02* (2013.01); *B05D 3/002* (2013.01); *B05D 3/06* (2013.01);
(Continued)

(58) Field of Classification Search
CPC .... G01N 33/689; G01N 33/558; G01N 33/76; G01N 33/525; B05D 1/02; B05D 3/002; B05D 3/06
(Continued)

(56) References Cited

U.S. PATENT DOCUMENTS 5,252,496 A   10/1993   Kang et al.
5,591,645 A    1/1997   Rosenstein
(Continued)

FOREIGN PATENT DOCUMENTS

EP       1291653 B1      6/2007

OTHER PUBLICATIONS

International Search Report and Written Opinion, PCT/EP2014/001151, dated Jul. 30, 2014.

*Primary Examiner* — Jyoti Nagpaul
(74) *Attorney, Agent, or Firm* — McDonald Hopkins LLC

(57) ABSTRACT

The present invention relates to a lateral flow membrane arrangement (1), comprising a microporous membrane layer (2) and a liquid-impermeable support layer (3), for lateral flow of a liquid through the microporous membrane layer (2), wherein the microporous membrane layer (2) is supported on the liquid-impermeable support layer (3) and has at least one detection zone (5) and at least one non-detection zone, wherein binding agents are immobilized in the at least one detection zone (5), the liquid-impermeable support layer (3) has at least one zone having a large thickness and at least one zone having a small thickness, the microporous membrane layer (2) is supported on the liquid-impermeable support layer (3) such that said at least one detection zone is provided above said at least one zone of the support layer having a large thickness and said at least one non-detection zone is provided above said at least one zone of the support layer having a small thickness, the zones are oriented in a (Continued)

direction orthogonally to the lateral flow direction (a) of said liquid, the detection zone (5) has a thickness (7) of 100 to 150 μm over the entire width of the membrane, the non-detection zone has a thickness (8) of at most 300 μm over the entire width of the membrane, and the lateral flow membrane arrangement (1) has a constant thickness (9), as well as to a lateral flow immunoassay device comprising said membrane arrangement (1).

17 Claims, 3 Drawing Sheets

(51) Int. Cl.
| | | |
|---|---|---|
| G01N 33/52 | (2006.01) | |
| G01N 33/558 | (2006.01) | |
| B05D 1/02 | (2006.01) | |
| B05D 3/00 | (2006.01) | |
| B05D 3/06 | (2006.01) | |
| G01N 33/76 | (2006.01) | |

(52) U.S. Cl.
CPC ......... *G01N 33/525* (2013.01); *G01N 33/558* (2013.01); *G01N 33/76* (2013.01); *G01N 2333/59* (2013.01)

(58) Field of Classification Search
USPC .......................................................... 422/69
See application file for complete search history.

(56) References Cited

U.S. PATENT DOCUMENTS

| | | | |
|---|---|---|---|
| 6,884,592 B2 | 4/2005 | Matzinger et al. | |
| 2005/0227370 A1* | 10/2005 | Ramel | C12Q 1/00 436/514 |
| 2006/0205059 A1 | 9/2006 | Esfandiari | |
| 2009/0291508 A1* | 11/2009 | Babu | B82Y 30/00 436/518 |
| 2010/0255512 A1 | 10/2010 | Wu et al. | |
| 2012/0184462 A1* | 7/2012 | O'Farrell | G01N 33/558 506/15 |
| 2013/0089858 A1* | 4/2013 | Wong, Jr. | G01N 33/54386 435/6.1 |
| 2015/0192575 A1* | 7/2015 | Van Amerongen | G01N 33/54386 422/69 |

* cited by examiner

LATERAL FLOW MEMBRANE ARRANGEMENT AND LATERAL FLOW IMMUNOASSAY DEVICE COMPRISING THE SAME

This application is a 35 U.S.C. 371 national stage filing and claims priority to PCT Application PCT/EP2014/001151 entitled "LATERAL FLOW MEMBRANE ARRANGEMENT AND LATERAL FLOW IMMUNOASSAY DEVICE COMPRISING THE SAME," filed Apr. 29, 2014, which claims the benefit of European Application 13003965.4 filed Aug. 8, 2013, each of which are incorporated by reference herein in their entirety.

FIELD OF THE INVENTION

The present invention relates to a lateral flow membrane arrangement comprising a microporous membrane layer supported on a liquid-impermeable support layer, and to a lateral flow immunoassay device comprising the same.

BACKGROUND OF THE INVENTION

In modern biochemical analytics, immunoassays are routinely used to detect the presence or concentration of various substances, often referred to as ligands or analytes, in biological fluids such as blood, urine or saliva. In a solid phase immunoassay, a binding agent, typically an antibody which is specific for the ligand to be detected, is immobilized on a solid support. A test fluid that may comprise the ligand to be detected is contacted with the solid support and a complex between the binding agent and the ligand is formed in case the ligand is present. In order to make the complex visible, labeled antibodies may be used that bind to the complex followed by visual detection of the labeled antibody bound to the complex.

U.S. Pat. No. 5,591,645 discloses a sandwich immunoassay, wherein a ligand is sandwiched between a labeled antibody and an antibody immobilized on a solid support.

Porous materials such as nitrocellulose, nylon, cellulose acetate, glass fibers and other porous polymers have been employed as solid supports in solid phase immunoassays. In so-called lateral flow assays, a fluid to be tested for the presence of a ligand is applied to one end of a porous membrane layer and flows in lateral direction through the membrane under the action of capillary forces. The porous membrane comprises an immobilized binding agent that is capable of binding the ligand to be detected. The immobilized binding agent may be evenly distributed over the entire membrane. Typically, however, the immobilized binding agent is located in defined test or detection zones in the membrane, usually in narrow test lines that have been applied by means of inkjet printing or other aerosol spraying techniques.

In lateral flow immunoassays, typically a thin layer of microporous material with immobilized binding agent is supported on a liquid-impermeable layer to provide sufficient rigidity to the fragile membrane layer. Usually a layer of microporous material with a thickness in the range of from about 100 to 200 μm is supported on a support layer, usually referred to as "membrane backing". However, depending on the requirements, the membrane thickness may be thinner than 100 or thicker than 200 μm.

Frequently occurring problems with lateral flow immunoassays relate to assay sensitivity and, associated therewith, signal intensity. Such assays are typically five to ten times less sensitive than for example an Enzyme-Linked Immuno Sorbent Assay (ELISA). Several measures to enhance the signal have been proposed, for example signal amplification strategies such as enzymatic enhancement of the signal, but there is still room for improvement.

Thus, the object underlying the present invention is to provide a lateral flow membrane arrangement resulting in an improved assay sensitivity and signal intensity.

DISCLOSURE OF THE INVENTION

It has now been found that the above object can be achieved by providing a lateral flow membrane arrangement, wherein a microporous membrane layer has at least one detection zone and at least one non-detection zone, wherein the detection zone has a smaller thickness than the non-detection zone, whereby the sensitivity and signal intensity of lateral flow immunoassays can be largely enhanced.

Accordingly, the present invention relates to a lateral flow membrane arrangement, comprising a microporous membrane layer and a liquid-impermeable support layer, for lateral flow of a liquid through the microporous membrane layer, wherein the microporous membrane layer is supported on the liquid-impermeable support layer and has at least one detection zone and at least one non-detection zone, wherein binding agents are immobilized in the at least one detection zone, the liquid-impermeable support layer has at least one zone having a large thickness and at least one zone having a small thickness, the microporous membrane layer is supported on the liquid-impermeable support layer such that said at least one detection zone is provided above said at least one zone of the support layer having a large thickness and said at least one non-detection zone is provided above said at least one zone of the support layer having a small thickness, the zones are oriented in a direction orthogonally to the lateral flow direction of said liquid, the detection zone has a thickness of 100 to 150 μm over the entire width of the membrane, the non-detection zone has a thickness of at most 300 μm over the entire width of the membrane, and the lateral flow membrane arrangement has a constant thickness.

The membrane arrangement can advantageously be applied in a solid phase lateral flow immunoassay.

An important advantage of having a detection zone with a smaller thickness than the non-detection zone, as adopted by the present invention, is that in the detection zones, the liquid to be analyzed is forced to flow through the part of the microporous membrane layer that comprises immobilized binding agents. This will result in an increased number of ligands having interaction with said immobilized binding agents and therewith the sensitivity of the immunoassay in terms of signal intensity is increased.

In a further aspect, the invention relates to a lateral flow immunoassay device comprising the membrane arrangement as hereinbefore defined.

In a still further aspect, the invention relates to the use of the above-described lateral flow membrane arrangement in an immunological pregnancy test.

DETAILED DESCRIPTION OF THE INVENTION

Figure 1:
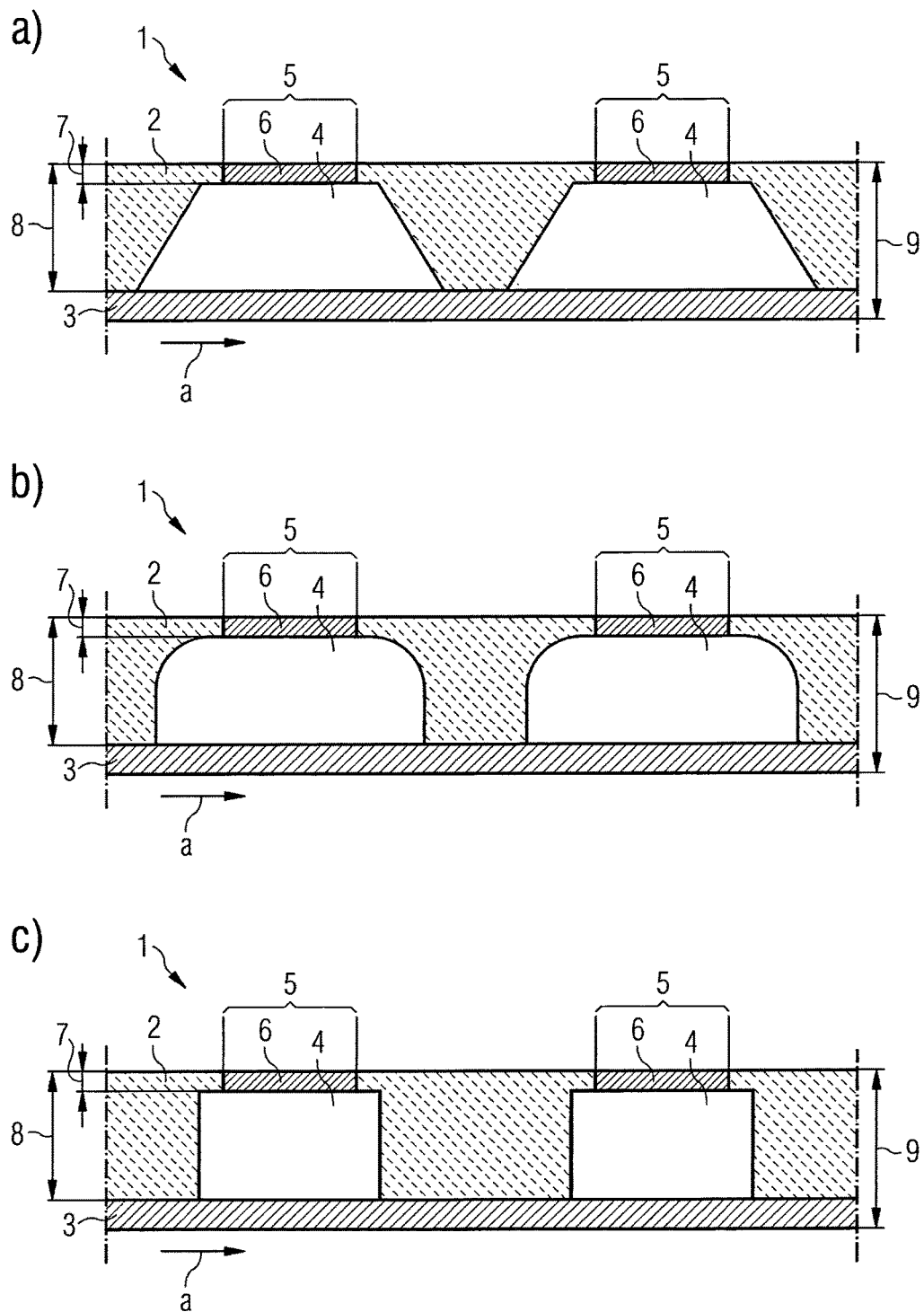
FIG. 1 shows longitudinal sections of lateral flow membrane arrangements according to the invention.

The lateral flow membrane arrangement according to the invention is an elongate arrangement of a microporous membrane layer supported on a liquid-impermeable support layer. The arrangement is suitable for lateral flow of a liquid through the membrane layer under the action of capillary forces and is typically used in lateral flow immunoassays for detecting a ligand or analyte in a test fluid that flows laterally through the microporous membrane layer. The elongate arrangement has a length, a width and a thickness or height. The thickness or height of the arrangement, i.e. support layer plus membrane layer, is constant. The membrane layer's detection zone has a thickness in the range of from 100 to 150 µm, preferably of from 100 to 130 µm, more preferably of from 110 to 120 µm, over the entire width of the membrane arrangement. However, in certain embodiments, the membrane layer's detection zone may have a thickness of less than 100 µm or of more than 150 µm.

In the membrane arrangement according to the invention, the membrane layer in the membrane arrangement has, in lateral direction, alternating the thickness of the detection zone and the thickness of the non-detection zone, which is larger than the thickness of the detection zone, each over the entire width of the membrane arrangement. The thickness of the membrane layer's non-detection zone is at most 300 µm, preferably in the range of from 100 to 250 µm, more preferably of from 150 to 250 µm, even more preferably of from 150 to 200 µm. Since the arrangement of membrane layer and support layer has a constant thickness, the support layer will decrease in thickness where the membrane layer increases in thickness and vice versa.

The thickness of the membrane layer may decrease and increase in any suitable way, for example stepwise or gradually. Preferably, the thickness of the membrane layer is gradually decreasing from the thickness of the detection zone to the thickness of the non-detection zone. Reference herein to gradually decreasing is to a decrease with a gradient and not stepwise, i.e. a decrease with a finite tangent (decrease in thickness per unit of length of membrane). More preferably, the thickness is decreasing with at most 300% (3 µm decrease in thickness over 1 µm membrane length), even more preferably with at most 200%, even more preferably the decrease is in the range of from 30 to 100%.

The membrane layer may be made of any suitable microporous material for lateral flow membranes. Such materials are known in the art and include nitrocellulose, nylon, cellulose acetate, glass fibers, cross-linked dextran and other porous polymers. Preferably, the membrane layer is a nitrocellulose layer. Nitrocellulose membrane layers for lateral flow assays are well-known in the art and are composed of interconnected nitrocellulose fibers.

The support layer is a liquid-impermeable support layer. Such support layers are well-known in the art and are often referred to as "backing". Suitable support layers include polymeric materials such as for example polyester, polypropylene, polyethylene, acrylic (co)polymers, vinylacrylic polymers, polycarbonates and heteropolysaccharides.

The membrane arrangement according to the invention is preferably used in a lateral flow immunoassay. In lateral flow immunoassays, a binding agent that is able to bind the ligand or analyte to be detected in the test fluid is immobilized in the microporous membrane layer through which the test fluid flows. Therefore, the membrane arrangement according to the present invention comprises binding agents immobilized in the at least one detection zone. Binding agents are known in the art and include for example antibodies and aptamers.

According to a preferred embodiment of the present invention, the binding agents are antibodies directed against hCG to be used in a pregnancy test.

Typically in lateral flow immunoassays, such binding agents are immobilized in the form of at least one test line or spot and often a control line or spot that is applied on the membrane layer by spraying techniques such as inkjet printing or other aerosol spraying techniques. The membrane layer then comprises at least one detection zone wherein binding agents are immobilized. Each detection zone may comprise at least one line or spot with immobilized binding agent. Thus, in the membrane arrangement according to the invention, the binding agent is immobilized in the membrane layer in at least one detection zone having the specified thickness.

In order to visualize the complex between the binding agent and the ligand formed in the detection zones, detectable markers such as for example immunolabels are typically used. Very often, the liquid to be analyzed first flows through a so-called conjugate pad before it flows through the lateral flow membrane. The conjugate pad comprises a moveable conjugate of detectable marker and a detection agent, i.e. an agent that can bind to the ligand and may be the same or different from the binding agent. If the liquid to be analyzed flows through the conjugate pad, the conjugate binds to the ligand and the ligand/conjugate complex flows with the liquid through the membrane layer. In the membrane layer the ligand-conjugate complex binds to immobilized binding agent. Alternative to a conjugate pad upstream of the lateral flow membrane, the lateral flow membrane may comprise at least one conjugate zone that comprises a moveable conjugate of detectable marker and detection agent. Such conjugate zones are preferably located upstream of a detection zone. If the membrane layer comprises at least one conjugate zone, it is preferred that the membrane layer has the same thickness in the at least one conjugate zone as in the at least one detection zone. Suitable detectable markers that can be used in this respect are not particularly limited and are known in the art. They include for example fluorescent dyes and gold nanoparticles.

In order to allow for improved binding of a ligand to binding agents in the detection zone(s) and, if present, to detection agents in the conjugate zone(s), it is preferred to have a relatively low flow velocity of liquid to be analyzed in the detection and conjugate zones. Therefore, the width of the membrane arrangement in detection and/or conjugate zones, wherein the membrane layer has the thickness of the at least one detection zone, i.e. a thickness in the range of from 100 to 150 µm, is preferably larger than the width of the membrane arrangement in zones wherein the membrane layer has the larger thickness of the at least one non-detection zone. More preferably, the width of the membrane arrangement in detection and/or conjugate zones having the thickness of the at least one detection zone is such that the flow velocity in such zones is equal or lower, preferably lower, than the flow velocity outside such zones. Preferably, the flow velocity in such zone is in the range of from 25 to 100%, more preferably of from 50 to 95% of the flow velocity outside such zones. Thus, the product of width of the membrane arrangement and thickness of the membrane layer in detection/conjugate zones is preferably not smaller than such product in zones with the thickness outside of the detection/conjugate zones.

The present invention further relates to a lateral flow immunoassay device comprising the membrane arrangement according to the invention. Lateral flow immunoassay devices are well-known in the art and are for example described in US2006/0205059, U.S. Pat. Nos. 5,252,496 and 5,591,645. The membrane arrangement may be used in any suitable lateral flow immunoassay device known in the art.

Typically, lateral flow immunoassay devices comprise a reaction zone comprising a lateral flow membrane with immobilized binding agents supported on a liquid-impermeable support layer, a sample addition zone upstream of the reaction zone and an absorbing zone downstream of the reaction zone. Reference herein to upstream or downstream is with respect to the direction of the lateral fluid flow. Test fluid is added to the sample addition zone that typically comprises a filter pad in which the liquid is absorbed. By the action of capillary forces, the liquid flows from the sample addition zone through the reaction zone to the absorbing zone. The device may comprise a so-called conjugate zone comprising moveable immunolabels or other detectable markers that are conjugated to a detection agent that binds to the ligand to be detected in the test liquid, between the sample addition zone and the reaction zone, so that test liquid is forced to flow through the conjugate zone. The labeled detection agents will then bind to the ligands in the test fluid and labeled ligands flow through the test zone and are bound to immobilized binding agents in the reaction zone where they can be visualized. Alternatively, the membrane layer comprises at least one conjugate zone as described hereinabove.

Preferably, the lateral flow immunoassay device according to the invention is a lateral flow immunoassay device comprising a microporous membrane layer comprising binding agents that are applied to the detection zone(s) by means of inkjet printing or another spraying technique.

The membrane arrangement according to the invention is preferably manufactured by first providing a liquid-impermeable support layer and then applying a solution of the material of which the membrane layer is composed in a suitable solvent on the support layer. The solvent is then evaporated and a membrane arrangement of a membrane layer supported on the support layer is obtained. A microporous membrane layer having the different thicknesses over its entire width in the detection zone(s) and non-detection zone(s) (and optionally in the conjugate zone(s) and non-conjugate zone(s)) is obtained by providing a liquid-impermeable support layer having elongate protrusions with a height that is similar to the difference in thickness between the detection zone(s) and non-detection zone(s) (and optionally the conjugate zone(s) and non-conjugate zone(s)) in the membrane layer to be obtained. In preferred embodiments, said protrusions are obtained by adhering strips of support layer material to a liquid-impermeable support layer having no protrusions, wherein said strips have a thickness that corresponds to the difference in thickness between the detection zones and non-detection zones. Alternatively, said protrusions are obtained by laser-etching a liquid-impermeable support layer having a thickness that corresponds to the thickness of the support layer in the detection zones. In a further embodiment, the method for the manufacture of the membrane arrangement according to the invention further comprises a step of applying the binding agent to the detection zones by inkjet printing or aerosol spraying.

In fact, the support layer acts as a mould for the membrane layer to be obtained. By applying the membrane material as a liquid solution, a membrane arrangement, i.e. membrane layer plus support layer, of a constant height is obtained. Elongate membrane arrangements according to the invention suitable to be used in lateral flow immunoassay devices, can be cut from the arrangement of support and membrane layers thus obtained.

Furthermore, the present invention provides the use of the above-described lateral flow membrane arrangement in an immunological pregnancy test, such that a pregnancy test having an improved assay sensitivity and signal intensity can be carried out. In this aspect, the binding agent is preferably an antibody directed against hCG.

FIG. 1 schematically shows longitudinal sections of examples for a lateral flow membrane arrangement 1 according to the invention comprising a microporous membrane layer 2 and a support layer 3. Support layer 3 has protrusions 4 which may have different shapes (a, b, c) over its entire width. Membrane layer 2 comprises detection zones 5 comprising binding agents immobilized in a zone carrying binding agents 6, and non-detection zones. Each detection zone 5 comprises a zone carrying binding agents 6. Membrane layer 2 has a thickness 7 in detection zones 5 and a thickness 8 outside the detection zones (in the non-detection zones). Upstream of each detection zone 5, the thickness of membrane layer 2 is decreasing from thickness 8 to thickness 7. Membrane arrangement 1 has a thickness 9 that is constant over the entire length of membrane arrangement 1. Reference herein to upstream is with reference to the lateral flow direction. Arrow 'a' indicates the flow direction.

The present invention is further illustrated by the following examples, without being limited thereto.

EXAMPLES

Example 1: Preparation of a Lateral Flow Membrane Arrangement

As a liquid-impermeable support layer, a polyester film (Melinex 400, crystal clear, slip-treated on one surface, manufactured by Pütz GmbH+Co. Folien KG, Taunusstein, Germany) having a thickness of 100 µm and dimensions of 30×50 cm was used. On said polyester film, strips having a width of 0.5 cm of a polyester film (Melinex 400, crystal clear, slip-treated on one surface, manufactured by Pütz GmbH+Co. Folien KG, Taunusstein, Germany) having a thickness of about 50 µm were adhered at a distance of 2.5 cm (measured from the center of the width direction of one strip to the center of the width direction of the next strip), such that the slip-treated surfaces of both the 100 µm liquid-impermeable support layer and the 50 µm strips were facing upward. As an adhesive for adhering said strips, Scotch Weld 49 (pressure-sensitive adhesive based on acrylate), manufactured by 3M, St. Paul, Minn., USA, was used (thickness of about 35 µm).

Then, a nitrocellulose solution (3 to 8% (wt) of nitrocellulose having a nitration grade of 12%, 35 to 45% (wt) of isopropanole, 40 to 50% (wt) of methyl acetate, and 7 to 13% (wt) of water) was applied on said support layer including the strips with a small doctor blade in the direction of the strips. The solution was applied at a thickness of 1200 µm and then dried for 45 min such that a lateral flow membrane arrangement having a microporous membrane with a thickness of the non-detection zone of 200 µm and a thickness of the detection zone of 115 µm was obtained (total thickness of the lateral flow membrane arrangement: about 300 µm). The obtained lateral flow membrane arrangement was finally cut into stripes with a width of 0.5 cm.

Example 2: Lateral Flow Assay

A membrane as prepared in Example 1 was modified for carrying out a lateral flow assay. A sample pad was fixed to the bottom end (Ahlstrom, Grade 6615). An absorbent pad was fixed to the top end (Ahlstrom; grade 222).

About 10 µl of a solution of anti beta-hCG gold conjugated antibody, OD 10 (Antibody: a) Standard gold FSH WHO 92/510 NIBSC, BBI International, Nr. hCG WHO 75/589; or as alternative b) monoclonal anti-beta hCG CGC clone 1, Arista Biologicals Nr. CGBCG-0701) in 100 mM Tris-HCl, pH 8.0 buffer was sprayed adjacent to the prefilter to the bottom end of the test strip. A test line comprising the capture antibody of the antigen specific antibody was pipetted in a horizontal line in a distance of about half the length from the bottom of the membrane strip. A control line comprising an antibody for a non-specific binding of other antibodies was pipetted upstream of the test line. Pipetting of test line and control line can be performed by means of an automated dispensing system or by hand.

The antibody of the testline was prepared as a 0.5 mg/ml solution of an anti-alpha hCG monoclonal goat anti alpha hCG (Arista Biologicals, Inc., Nr. ABACG-0500) in a buffer of 5 mM borax, 150 mM sodium chloride, pH 8.0. The antibody of the control line comprised 1.25 mg/ml of an anti-mouse IgG from goat (Alchemy Laboratories Ltd, Nr. 143) in a buffer of 5 mM borax, 150 mM sodium chloride, pH 8.0.

Figure 3:
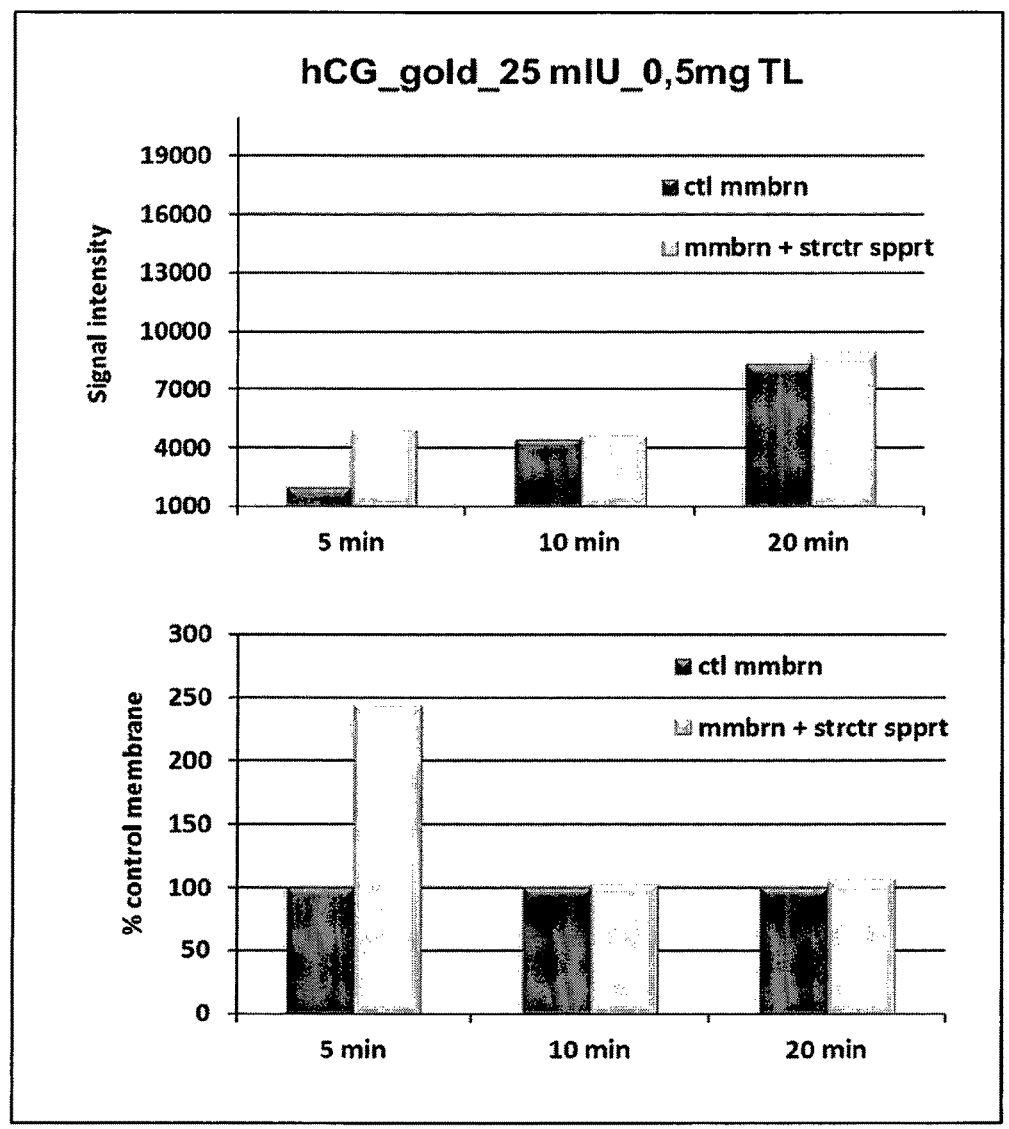
FIG. 3 shows further results of a signal intensity quantification of the lateral flow membrane arrangement used in Example 3.

The membrane carrying the antibodies was then incubated with a liquid probe in order to determine whether the antigen (in the particular case human chorionic gonadotropin) is present. Incubation can take place by putting the membrane strip loaded with the antibodies as specified above with its sample pad into a droplet of the liquid probe, and keeping it therein in an upright position until the liquid frontier line has reached the absorbent pad. The liquid probe comprises the antigen if both the test line and the control line exhibit a red color (FIG. 3, top). The liquid probe does not comprise the antigen if only the control line turns coloured. The test is not working if the control line does not light up. The intensity of the colour can be inspected by the naked human eye or preferably by a publicly available Lateral Flow Reader (Skannex AS).

Example 3: Structured Membrane

Two test strips comprising a membrane (control; structured membrane) have been incubated according to the method of Example 2.

The structured membrane has been prepared in accordance with Example 1.

The control (unstructured) membrane is composed of a 100 µm thick support layer, a polyester film (Melinex 400, crystal clear, slip-treated on one surface, manufactured by Pütz GmbH+Co. Folien KG, Taunusstein, Germany) with a nitrocellulose membrane layer of 160 µm thickness casted in the same way as in Example 1.

The concentration of the gold labeled antibody was 50 mIU (FIG. 3) or 25 mIU (FIG. 4). The test line antibody was applied in an amount of 0.5 mg onto said control membrane (continuous nitrocellulose of constant thickness) and to the structured membrane.

The diagrams of FIGS. 3 and 4 are depicting the results of several independent experiments in a time dependent manner.

Figure 2:
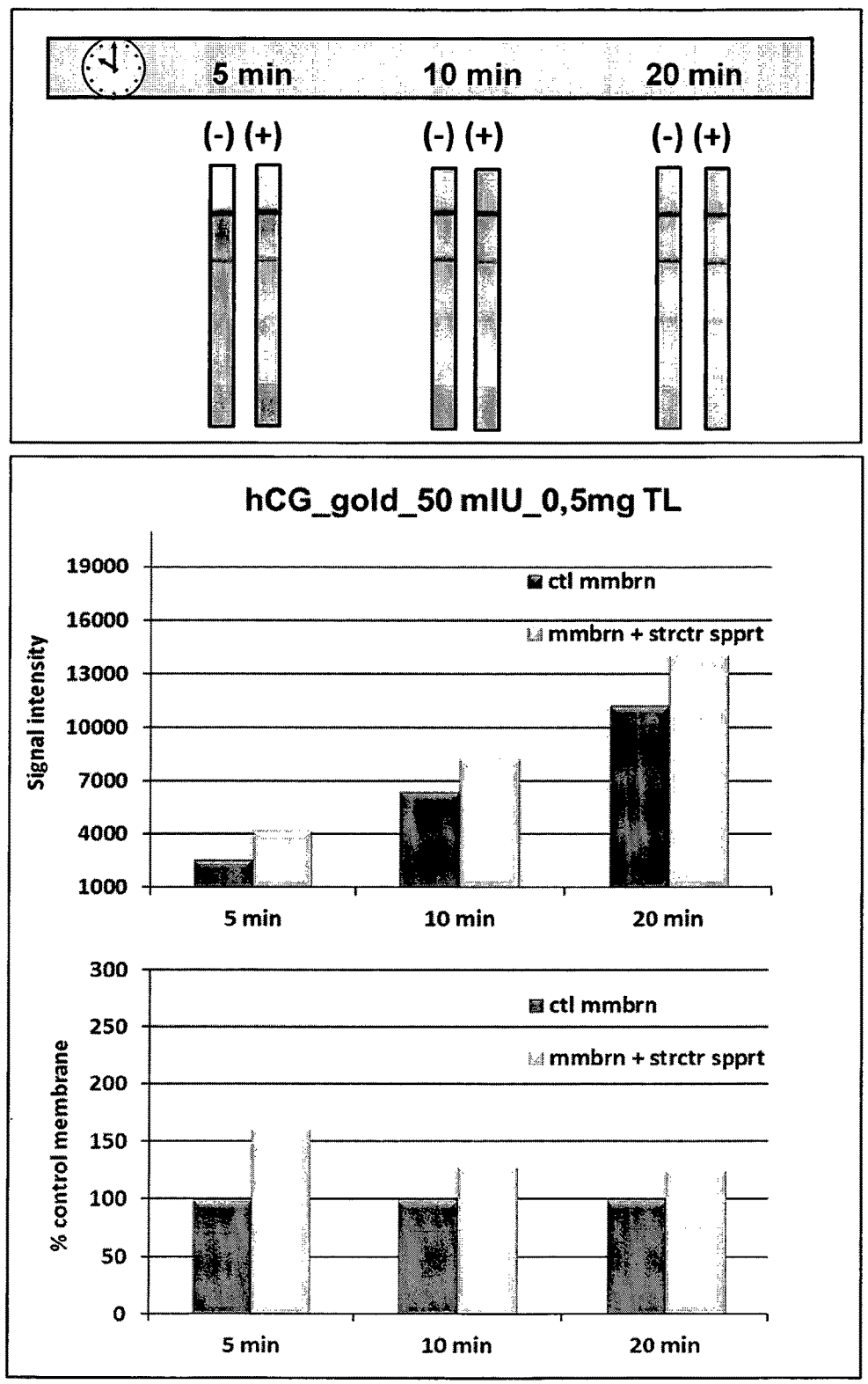
FIG. 2 shows the results of a signal intensity quantification of the lateral flow membrane arrangement used in Example 3.

The left column for each point in time is always representing the control membrane, whereas the right column is showing the result of the structured membrane. The signal intensity output coming from the structured membrane approach is in all cases higher than that one coming from the control membrane. This is particularly true for a shortened time of incubation (FIG. 2 and FIG. 3; 5 min).

The conclusion from these results is that a structured membrane is exhibiting a better signal intensity for a given set of antigen and antibody. A better signal intensity has different implications such as a diminished risk of false positives which may be a burden for a patient e.g. when searching for a disease (cancer) or in case of a pregnancy test.

Furthermore the incubation time can be shortened. An antigen can be detected at a lower concentration leading to the effect that the marker of a physiological parameter or disease a disease is detectable much earlier.

There is also the possibility to use less antibodies for gaining the same effect which may be of huge value for expensive material.

The following reference signs are used in the present application:
(1) Lateral flow membrane arrangement
(2) Microporous membrane layer
(3) Liquid-impermeable support layer
(4) Protrusion of the liquid-impermeable support layer
(5) Detection zone
(6) Zone carrying binding agents
(7) Thickness of detection zones
(8) Thickness of non-detection zones
(9) Thickness of the lateral flow membrane arrangement

The invention claimed is:

1. A lateral flow membrane arrangement, comprising a microporous membrane layer and a liquid-impermeable support layer, for lateral flow of a liquid through the microporous membrane layer, wherein
the microporous membrane layer is supported on the liquid-impermeable support layer and has at least one detection zone and at least one non-detection zone, wherein binding agents are immobilized in the at least one detection zone,
the liquid-impermeable support layer has at least one zone having a first thickness and at least one zone having a second thickness, the second thickness being smaller than the first thickness,
the microporous membrane layer is supported on the liquid-impermeable support layer such that said at least one detection zone is provided above said at least one zone of the support layer having the first thickness and said at least one non-detection zone is provided above said at least one zone of the support layer having the second thickness,
the zones are oriented in a direction orthogonally to the lateral flow direction (a) of said liquid,
the detection zone has a thickness of 100 to 150 µm over the entire width of the membrane,
the non-detection zone has a thickness of at most 300 µm over the entire width of the membrane, and
the lateral flow membrane arrangement has a constant thickness.

2. The lateral flow membrane arrangement according to claim 1, wherein the microporous membrane layer is made of nitrocellulose.

3. The lateral flow membrane arrangement according to claim 1, wherein the binding agents are antibodies directed against hCG.

4. The lateral flow membrane arrangement according to claim 1, wherein the detection zone has a thickness from 100 to 130 µm.

5. The lateral flow membrane arrangement according to claim 1, wherein the non-detection zone has a thickness in the range of from 100 to 250 µm.

6. The lateral flow membrane arrangement according to claim 1, wherein the thickness of the microporous membrane layer is stepwise decreasing in the lateral flow direction from the non-detection zone to the detection zone and is stepwise increasing in the lateral flow direction from the detection zone to the non-detection zone.

7. The lateral flow membrane arrangement according to claim 1, wherein the thickness of the microporous membrane layer is gradually decreasing in the lateral flow direction from the non-detection zone to the detection zone and is gradually increasing in the lateral flow direction from the detection zone to the non-detection zone.

8. The lateral flow membrane arrangement according to claim 1, wherein the microporous membrane layer further comprises at least one conjugate zone comprising a moveable conjugate of a detection agent and a detectable marker, wherein said at least one conjugate zone is provided on the liquid-impermeable support layer in the same manner as the at least one detection zone and has the same thickness as the at least one detection zone.

9. The lateral flow membrane arrangement according to claim 1, wherein the width of the lateral flow membrane arrangement is larger in the at least one detection zone and in the at least one conjugate zone than outside the detection and conjugate zones.

10. A lateral flow immunoassay device comprising the lateral flow membrane arrangement according to claim 1.

11. An immunological pregnancy test comprising the lateral flow membrane arrangement according to claim 1.

12. A method for the manufacture of a lateral flow membrane arrangement according to claim 1, comprising the steps of:
(a) providing a liquid-impermeable support layer having elongate protrusions with a height that corresponds to the difference in thickness between the detection zones and non-detection zones;
(b) applying a solution of the material of which the membrane layer is composed in a suitable solvent onto the support layer; and
(c) evaporating the solvent.

13. The method according to claim 12, wherein said protrusions are obtained by adhering strips of support layer material to a liquid-impermeable support layer having no protrusions, wherein said strips have a thickness that corresponds to the difference in thickness between the detection zones and non-detection zones.

14. The method according to claim 12, wherein said protrusions are obtained by laser-etching a liquid-impermeable support layer having a thickness that corresponds to the thickness of the support layer in the detection zones.

15. The method according to claim 12, further comprising the step of:
(d) applying the binding agent to the detection zones by inkjet printing or aerosol spraying.

16. The lateral flow membrane arrangement according to claim 1, wherein the non-detection zone has a thickness in the range of from 150 to 250 µm.

17. The lateral flow membrane arrangement according to claim 1, wherein the non-detection zone has a thickness in the range of from 150 to 200 µm.

* * * * *